United States Patent [19]
Kerrigan

[11] Patent Number: 6,001,775
[45] Date of Patent: Dec. 14, 1999

[54] FERTILIZER COMPOSITION WITH HERBICIDE

[76] Inventor: Kurt J. Kerrigan, 1311 SE. 9th Ave., Pompano Beach, Fla. 33060

[21] Appl. No.: 09/235,184

[22] Filed: Jan. 22, 1999

Related U.S. Application Data

[63] Continuation of application No. 08/916,872, Aug. 22, 1997, abandoned.

[51] Int. Cl.$^6$ .............................. A01N 43/66; A01N 43/68
[52] U.S. Cl. ........................... 504/227; 504/231; 504/232
[58] Field of Search ..................................... 504/110, 101, 504/227, 231, 232

[56] References Cited

U.S. PATENT DOCUMENTS

| | | | |
|---|---|---|---|
| 4,015,970 | 4/1977 | Hennart | 71/11 |
| 4,929,273 | 5/1990 | Takematsu et al. | 71/116 |
| 5,466,274 | 11/1995 | Hudson et al. | 71/28 |

FOREIGN PATENT DOCUMENTS

| | | |
|---|---|---|
| 60190701 | 3/1984 | Japan . |
| 9526942 | 10/1995 | WIPO . |

*Primary Examiner*—Jose' G. Dees
*Assistant Examiner*—Alton Pryor
*Attorney, Agent, or Firm*—Robert M. Downey, P.A.

[57] ABSTRACT

A fertilizer composition is provided in the form of a water soluble tablet structured to disintegrate and release into a stream of water at a predetermined rate, the composition including: N-P-K components of a desired ratio including 10.0 to 40.0% by weight of a nitrogen containing component, 0.0 to 40.0% by weight of a potassium containing component and 0.0 to 40.0% by weight of a phosphorus containing component; a binder in an amount of between 6.0% to 15.0% by weight; an s-triazine type herbicide in an amount of between 0.05% to 2.0% by weight; and inert components, wherein the amount of components in the composition totals 100%.

2 Claims, No Drawings

FERTILIZER COMPOSITION WITH HERBICIDE

This is a continuation patent application based on patent application Ser. No. 08/916,872 filed on Aug. 22, 1997 now abandoned.

BACKGROUND OF THE INVENTION

1. Field of the Invention

The present invention relates to fertilizer compositions and, more particularly, to a dry, water dispersible tablet containing a fertilizer, a herbicide and a binding agent wherein the tablet is structured to disintegrate when subjected to a stream of water so that the composition is released into the water stream at a predetermined rate and concentration.

2. Description of the Related Art

Lawns, plants, botanicals and other plant life require watering, fertilizing and treatment with herbicides and pesticides on a regular scheduled regime in order to maintain health and promote growth. Typically, watering, fertilizing and herbicide treatment are performed as two or three separate operations. In some instances, spray devices may be used on a garden hose to simultaneously water and fertilize plants and flowers, or to apply a diluted herbicide or pesticide solution. During this application method, which is normally performed manually, the applied solution is quickly dispersed at uneven levels of distribution. Subsequent fertilization or weed control treatment is often neglected, as this application process is time-consuming and expensive.

Small fertilizer pellets for slow release in the soil, near the base of a plant, are well known and widely used in the related field. However, pellets of this type do not provide herbicides for lawns, shrubs and botanicals. While liquid "weed and feed" compositions are known and used in spray applicators, they disperse quickly, consuming large amounts of chemicals with each application. Furthermore, use of such spray applicators often results in uneven distribution of chemicals, with higher levels of fertilizer and herbicides in some areas than others, causing the roots of plants and lawns to be burned and damaged. It is, therefore, expensive, time-consuming and potentially hazardous to perform regular weed control treatment of lawns, plants, and botanicals using the present application methods and compositions.

In spite of the numerous fertilizer products presently available on the market, there still exists a need for a fertilizer composition containing a herbicide which can be released slowly, at a controlled rate, into a stream of flowing water so that lawns, plants and botanicals can be simultaneously watered, fed with fertilizer, and treated for weeds during regular watering operations.

SUMMARY OF THE INVENTION

The present invention provides a novel fertilizer composition which contains a herbicide and a binding agent. The composition is structured for slow release into a stream of flowing water in accordance with a predetermined rate of disintegration and concentration level. In a preferred embodiment, the fertilizer composition is provided in the form of a dry, water dispersible tablet and is suited for use in the chemical application method set forth in my pending patent application Ser. No. 08/861,591 filed on May 21, 1997.

The fertilizer composition includes N-P-K components, provided at any desired ratio, as well as a binder agent and a herbicide. In a preferred embodiment, the N-P-K components include ammonium sulfate in an amount of between 10 to 40% by weight of the composition, potassium sulfate in an amount of between 0 to 40% by weight of the composition and calcium phosphate monobasic in an amount of between 0 to 40% by weight of the composition. Ammonium phosphate may be substituted for ammonium sulfate and calcium phosphate monobasic to provide the desired N-P level. In a preferred embodiment, the binder agent is calcium carbonate, present in an amount of between 6 to 1 5% by weight of the composition, and the herbicide is an s-triazine type, such as 2-chloro-4-ethylamino-6-isopropylamine-s-triazine, and is present in an amount of between 0.05% to 2.0% by weight of the composition.

OBJECTS AND ADVANTAGES OF THE INVENTION

It is a primary object of the present invention to provide a fertilizer composition which contains a herbicide for application to various plant life including lawns, plants, and botancials, wherein the three operations of watering, feeding (fertilizing) and treatment for weeds is carried out simultaneously when applying the composition to the plant life.

It is a further object of the present invention to provide a fertilizer composition containing a herbicide which is structured for slow release of fertilizer and the herbicide, in accordance with a predetermined concentration and rate of release, into a stream of water during normal plant watering.

It is still a further object of the present invention to provide a fertilizer composition providing any desired N-P-K ratio and a herbicide for simultaneous watering, feeding and treatment of weeds during watering of plant life.

It is yet a further object of the present invention to provide a fertilizer composition containing a herbicide wherein the composition is provided in a dry, soluble tablet which is useful in an irrigation system for automated, systematic watering, feeding and weed treatment of plant life on a scheduled cycle.

It is still a further object of the present invention to provide a fertilizer composition containing a herbicide and wherein the composition is provided in a dry, water dispersible tablet and further wherein the composition includes a binder component for controlling a rate of disintegration of the tablet and release of the fertilizer and herbicide when exposed to a stream of flowing water.

These and other objects and advantages of the present invention will be more readily apparent with reference to the following detailed description.

DETAILED DESCRIPTION OF THE PREFERRED EMBODIMENTS

According to the present invention, the above objects and advantages are achieved by combining desired levels of N-P-K fertilizer with a herbicide and binder component. The composition may further include a lubricating component containing vegetable oil as a mold release agent to facilitate release of manufactured tablets from the manufacturing molds. Other inerts for anti-sticking, slow disintegration and binding of the composition in a tablet form may be provided, as set forth below.

In a preferred embodiment, the N-P-K fertilizer includes ammonium sulfate, potassium sulfate, and calcium phosphate monobasic. Alternatively, ammonium phosphate can be substituted for ammonium sulfate and calcium phosphate monobasic to provide the desired nitrogen and phosphorus levels.

The herbicide used in the composition, in the preferred embodiment, is Atrazine, 2-chloro-4-ethylamino-6-isopropylamine-s-triazine, manufactured and marketed under the trade names AAtrex, Atranex, Gesaprim, and Primatol A. Atrazine is an oily component and, when used in the composition of the present invention, appears to act as a water repellant to slow down the disintegration and dissolution of the pellet. Atrazine, according to studies conducted to date, also appears to be compatible and chemically stable, thereby providing for a long shelf-life of the composition. While Atrazine is used in one preferred embodiment, any s-triazine type herbicide, or other herbicides, are contemplated for use in the composition of the present invention.

The binder component of the composition is primarily comprised of calcium. In a preferred embodiment, calcium carbonate is used as the binder component. Huber 040-2007 manufactured by J. M. Huber Corporation is an example of a calcium carbonate product useful as the binder component in the composition. Other sources of ground limestone with the optimum particle size distribution can be substituted.

Lubritab, manufactured by Edward Mendell Co., is an example of a mold release agent useful in the composition to facilitate release of the manufactured tablet from a mold during manufacturing of tablets. Lubritab consists of partially hydrogenated vegetable and cottonseed oils. It also provides water repellency which slows down pellet dissolution. Other oils, particularly vegetable oil products, are useful as a mold release agent in the composition.

The following examples are presented in order to provide a fuller understanding of the composition of the present invention and the manner of preparation, and are, therefore, not intended to limit the scope of the invention.

EXAMPLE 1

| Component | Weight | Wt. Percent* |
|---|---|---|
| Ammonium Phosphate (Milled)** | 16.7 lbs | 25.0% |
| Potassium Sulfate (Sulfated Potash)*** | 16.7 lbs | 25.0% |
| Preblend (containing Atrazine)**** | 20.7 lbs | 31.5% |
| Calcium carbonate (Huber 040–200) | 6.0 lbs | 8.5% |
| Lubritab (Milled) | 6.7 lbs | 10.0% |
| Total: | 66.8 lbs | 100.0% |

*For a variation of the N-P-K levels, the ammonium phosphate (or sulfate) and potassium sulfate (or carbonate) quantities may be varied to any percent relative to the the values above (for example, the amount of ammonium phosphate could be 1 lb, 10 lbs or 50 lbs to form other N-P-K levels). The calcium carbonate and Lubritab may need to be adjusted to obtain optimum cohesion. No significant reaction between the phosphate, sulfate, or carbonate with the Atrazine is likely to occur with normal storage in the dry state. However, the preblend should be used immediately.
**Ammonium sulfate and calcium phosphate monobasic may be substituted for an equivalent amount of ammonium phosphate.
***Potassium carbonate may be substituted for an equivalent amount of potassium sulfate.
****Preblend: Consists of 57.14% triple superphosphate (milled), 40.32% Huber 040–200, and 2.54% liquid Atrazine.

Preparation of the embodiment of Example 1 involves combining the ammonium phosphate, potassium sulfate, Atrazine and calcium carbonate and tumble blending for two minutes. Thereafter, the mixture is bar blended for 30 seconds. Tumble blending is then resumed for one minute. Thereafter, Lubritab is combined to the mixture and the entire mixture is tumble blended for an additional five minutes. The resultant mixture is discharged into tablet molds and subjected to high pressure to produce hard tablets. In accordance with standard tablet manufacturing methods in the industry, for producing dry water soluble or dispersible tablets, such as dry chlorine tablets, the mixture is compressed from 2.2" in height to 1" in height, producing 120 gram tablets.

In the above example, the referred to preblend is a mixture prepared for convenience and dilution purposes to provide an even distribution of ingredients, and particularly the active ingredients. The preblend contains 2.54% liquid Atrazine. In the entire composition, Atrazine is present in the amount of between 0.05% to 2% by weight. Triple superphosphate, in the preblend, is primarily calcium phosphate produced by the action of phosphoric acid on phosphate rock.

The composition of Example 1 was tested for rate of disintegration, wherein it was determined that the application rate of pounds of nitrogen ranged between 0.25 to 2.5 lbs per 1,000 square feet. The actual weight of tablets required for the above range varies from 1 lb. (4 tablets) to 10 lbs. (40 tablets) depending on the level of nitrogen required.

Another example of the composition of the present invention is as follows:

EXAMPLE 2

| Component | Weight % | Comments |
|---|---|---|
| Calcium carbonate | 12.0% | Milled 1–4, –30 mesh. |
| Ammonium sulfate | 25.0% | Commercial grade |
| Potassium sulfate | 25.0% | Commercial grade |
| Ca Tripolyphosphate | 16.0% | Commercial grade |
| Dicalcium phosphate (DH) | 10.8% | Preblend w. Atrazine |
| Atrazine | 0.3% | Commercial grade |
| Methocel A15C | 9.0% | Thoroughly mix |
| Guar Gum | 0.2% | To slow disintegration |
| Talc | 1.5% | Anti-sticking, add later |
| Graphite | 0.2% | Lubricant, add later |
| Total: | 100.0% | |

The above composition is prepared by first mixing all components with the exception of talc and graphite. After thoroughly mixing the first eight components, the talc and graphite are added and mixed by tumble blending. The resultant composition mixture is thereafter deposited in tablet molds and compressed 2.2" in height to 1" in height to yield 120 gram tablets.

The manufactured tablets, comprised of the composition of the present invention, are primarily intended for use in a chemical delivery system of the type including a main water delivery line for directing a pressurized flow of water from a water source to one or more water discharge devices, as commonly found in an irrigation system (e.g., a sprinkler system). An air tight chamber is filled with a predetermined amount of the dry, water dispersible tablets. A water input line connects from a first location along a main water delivery line to the chamber containing the tablets, and a water output line connects from the chamber to a second location along the main water delivery line. The pressure of water flowing through the main water delivery line is higher at the first location than at the second location, causing a portion of the water flow to be diverted through the input line, into the chamber, through the output line, and feeding back into the main water delivery line at the second location. As water flows through the chamber, the dry water dispersible tablets, containing the composition of the present invention, gradually disintegrate causing a slow, controlled release of the N-P-K fertilizer and insecticide into the water flowing through the main water delivery line. This mixture is then directed to one or more discharge devices (e.g., sprinkler heads, spray nozzles, remote sprinklers, and the like) for application onto plant life, including lawns, plants, and botanicals.

While the instant invention has been described in accordance with various preferred embodiments thereof, it is recognized that departures may be made within the spirit and scope of the present invention which, therefore, should not be limited except as defined by the following claims as interpreted under the doctrine of equivalents.

Now that the invention has been described,
What is claimed is:

1. A fertilizer composition comprising:
   a nitrogen containing component selected from ammonium sulfate and ammonium phosphate in an amount of between 10.0% and 40.0% by weight of the composition;
   potassium sulfate in an amount of between 0.01% and 40.0% by weight of the composition;
   a phosphorus containing component selected from calcium phosphate and ammonium phosphate in an amount between 0.01% and 40.0% by weight of the composition;
   2-chloro-4-ethylamino-6-isopropylamine-s-triazine present in an amount of between 0.5% and 2.0% by weight of the composition;
   a binder in an amount of between 6.0% and 15.0% by weight of the composition containing calcium carbonate, said binder component being structured and disposed for controlling a rate of disintegration of the tablet and release of the composition into a stream of flowing water.

2. A fertilizer composition comprising:
   ammonium sulfate in an amount of between 10.0% and 40.0% by weight of the composition;
   potassium sulfate in an amount of between 0.01% and 40.0% by weight of the composition;
   calcium phosphate monobasic in an amount of between 0.01% and 40.0% by weight of the composition;
   a binder in an amount of between 6.0% and 15% by weight of the composition containing calcium carbonate and being structured and disposed for holding the composition in the form of an integral tablet and for controlling a rate of disintegration of the tablet and release of the composition into a stream of flowing water;
   a herbicide consisting of 2-chloro-4-ethylamino-6-isopropylamine-s-trazine in an amount of between 0.5% and 2.0% by weight of the composition; and a mold release agent to facilitate release of the integral tablet from a mold.

* * * * *